United States Patent
Ng

(10) Patent No.: US 12,097,147 B2
(45) Date of Patent: Sep. 24, 2024

(54) EYEDROP CONTAINER ADAPTER

(71) Applicant: Fletcher Jun Hao Ng, Manning (AU)

(72) Inventor: Fletcher Jun Hao Ng, Manning (AU)

( * ) Notice: Subject to any disclaimer, the term of this patent is extended or adjusted under 35 U.S.C. 154(b) by 0 days.

(21) Appl. No.: 18/518,494

(22) Filed: Nov. 23, 2023

(65) Prior Publication Data
US 2024/0091060 A1 Mar. 21, 2024

(51) Int. Cl.
*A61F 9/00* (2006.01)

(52) U.S. Cl.
CPC .................................. *A61F 9/0026* (2013.01)

(58) Field of Classification Search
CPC ...................................................... A61F 9/0026
See application file for complete search history.

(56) References Cited

U.S. PATENT DOCUMENTS

| | | | | |
|---|---|---|---|---|
| 4,002,168 | A * | 1/1977 | Petterson | B65D 23/003 222/421 |
| 6,041,978 | A * | 3/2000 | Hagele | A61F 9/0026 604/296 |
| 6,129,248 | A * | 10/2000 | Hagele | A61F 9/0008 222/571 |
| 6,135,985 | A * | 10/2000 | Fromer | A61F 9/0008 604/295 |
| 2013/0140225 | A1 * | 6/2013 | Decock | B05B 11/007 422/509 |
| 2015/0290029 | A1 * | 10/2015 | Wei | A61F 9/0008 514/75 |
| 2020/0276048 | A1 * | 9/2020 | Hossain | A61F 9/0026 |

FOREIGN PATENT DOCUMENTS

WO    WO-2007118124 A2 * 10/2007 ........... A61F 9/0008

OTHER PUBLICATIONS

Wang YM, Ren YL, Xu J, Zhang XF. Research and correlation analysis on the dripper contamination of carteolol hydrochloride eye drops. Ann Palliat Med 2021; 10(6):6779-6785. doi: 10.21037/apm-21-1237 (Year: 2021).*

* cited by examiner

*Primary Examiner* — Jessica Arble
*Assistant Examiner* — Arjuna P Chatrathi

(57) ABSTRACT

The invention presents a universal eyedrop adapter designed for efficient and hygienic eye drop administration. The adapter features a one-way valve at the top to prevent backflow, a reduced internal lumen to minimize drop wastage, and a controlled flow design for precise dispensing. The base incorporates spiral grooves for a secure fit and to prevent outflow. Constructed with an antimicrobial material, the adapter is bug-resistant, ensuring a clean application process. The ergonomic design includes a bent angle and a rounded tip to mitigate the risk of eye injury. The administration process involves attaching the adapter to most eyedrop containers, cleaning it and the receiving periorbital region with a sterile wipe, squeezing to dispense a drop at the rounded tip, and then touching the lateral canthus. The user blinks to utilize surface tension and a lateral-to-medial movement, bringing the drop onto the ocular surface.

9 Claims, 3 Drawing Sheets

EYEDROP CONTAINER ADAPTER

TECHNICAL FIELD

The present disclosure relates to the field of medical devices, and more specifically, systems and methods for ophthalmic care and the administration of ocular therapeutic agents.

BACKGROUND

The following description includes information that may be useful in understanding the present disclosure. It is not an admission that any of the information provided herein is prior art or relevant to the presently claimed disclosure, or that any publication specifically or implicitly referenced is prior art.

In the realm of ophthalmic care, advancements in medical devices play a pivotal role in enhancing the effectiveness and user experience of essential treatments. One such critical facet is the administration of eye drops, a routine yet vital practice in eye care. The conventional methods of eye drop application often face challenges related to hygiene, precision, and user safety.

Existing eyedrop administration methods may be susceptible to issues related to hygiene and contamination. Ensuring the sterility of the eyedrop solution is crucial to prevent infections or adverse reactions. Traditional eyedrop containers often result in wastage due to difficulties in administering the eye drops. The invention aims to reduce this wastage, ensuring that each drop is effectively utilized, which can be particularly important for expensive or limited-supply ocular therapeutic agents.

Different eyedrop containers on the market may have varying designs, but most users find it difficult to administer the eyedrops. This invention addresses this by providing a versatile adapter that accommodates different container shapes and sizes. The potential for accidental injury during eyedrop administration process is a consideration. The invention incorporates features to minimize the risk of eye injury, enhancing overall safety and user comfort during application.

The need for a controlled and efficient method of dispensing eye drops is evident. The invention's features, such as a controlled flow design, contribute to a more efficient and user-friendly administration experience.

As a result, there exists a need for a new device to aid eye drop administration, thus improving compliance and effectiveness of the ocular therapeutic agent.

OBJECTS OF THE PRESENT DISCLOSURE

The object of the invention is to provide a universal eyedrop container adapter that addresses various challenges associated with eye drop administration.

SUMMARY OF THE DISCLOSURE

The universal eyedrop adapter is an innovative device designed to enhance the efficiency, hygiene, and safety of eye drop administration. Its multifaceted features make it a comprehensive solution for users of various eyedrop containers.

The eyedrop adapter comprises of a one-way valve positioned at the top of the adapter to prevent backflow. An internal lumen with a decreasing diameter minimizes wastage of drops during administration, thus optimizing the utilization of the ocular therapeutic agent. A controlled flow design mechanism allows precise control over the dispensing of drops and preventing wastage during application. Spiral grooves at the base of the adapter ensure a secure attachment to various eyedrop containers and prevents unintended outflow, thereby minimizing the risk of leaks. A bent angle is incorporated into the design to mitigate the risk of eye injury during the administration process, prioritizing user safety and a flat rounded tip is designed to enhance user safety.

The inclusion of a one-way valve at the top of the adapter is a crucial aspect of the design, effectively preventing backflow and maintaining the sterility of the eyedrop solution. This feature ensures that any unused solution remains uncontaminated within the container.

To address the issue of drop wastage, the adapter incorporates a narrowing internal lumen. This design choice minimizes the amount of solution trapped within the dead space, promoting cost-effectiveness and reducing the volume of ocular therapeutic agent that would not be utilized.

The controlled flow design is another noteworthy feature, providing users with the ability to precisely regulate the dispensing of drops. This not only contributes to the overall efficiency of the device but also reduces the likelihood of accidental spillage, enhancing user convenience.

The spiral grooves at the base of the adapter serve a dual purpose. Firstly, they facilitate a snug fit on a variety of eyedrop containers, ensuring compatibility across different brands and designs. Secondly, these grooves act as a safeguard against outflow from the base, preventing leaks and maintaining a clean administration process.

Constructed from a antimicrobial material, the adapter mitigates risk of contamination during storage or use. This choice of material aligns with the overall emphasis on hygiene, contributing to the device's suitability for maintaining ocular health. The soft nature of silicone provides protection against potential trauma to the ocular surface, thus enhancing the safety profile of this device.

In terms of user safety, the adapter incorporates a bent angle and a rounded tip. These design elements minimize the risk of eye injury during the administration process, prioritizing user comfort and well-being.

The process of administration is streamlined and user-friendly. The adapter easily attaches to most eyedrop containers, and its surface and the receiving periorbital region can be cleaned with a sterile wipe to maintain a sterile environment. The user will squeeze the eye drop container, allowing a drop to appear at the rounded tip. To enhance the effectiveness of the device, the recipient's head can be postured by turning or tilting, placing the receiving eye in a superior position relative to the fellow eye to enable gravitational flow towards the ocular surface. The user will then bring the eye drop container and adapter to the face, touching the lateral canthus of the receiving eye. The user then blinks, utilizes surface tension, gravity, and eyelid movement to bring the drop onto the ocular surface.

In conclusion, the universal eyedrop container adapter combines a range of features to provide an effective solution for eyedrop administration. Its emphasis on hygiene, efficiency, and user safety makes it a valuable tool for individuals seeking an improved and convenient method for applying eye drops.

The summary of the disclosure does not necessarily disclose all the features essential for defining the disclosure. The disclosure may reside in a sub-combination of the disclosed features. The various combinations and sub-combination are fully described in the detailed description.

BRIEF DESCRIPTION OF DRAWINGS

The accompanying drawings are included to provide a further understanding of the present disclosure and are incorporated in and constitute a part of this specification. The drawings illustrate exemplary embodiments of the present disclosure and, together with the description, serve to explain the principles of the present disclosure.

The diagrams are for illustration only, which thus is not a limitation of the present disclosure, and wherein.

DETAILED DESCRIPTION OF DRAWINGS

To make the objectives, technical solutions, and advantages of this application clearer, the following clearly and completely describes the technical solutions in this application with reference to accompanying drawings in this application. The described embodiments are a part rather than all of embodiments of this application. All other embodiments obtained by a person of ordinary skill in the art based on embodiments of this application without creative efforts shall fall within the protection scope of this application.

Figure 1:
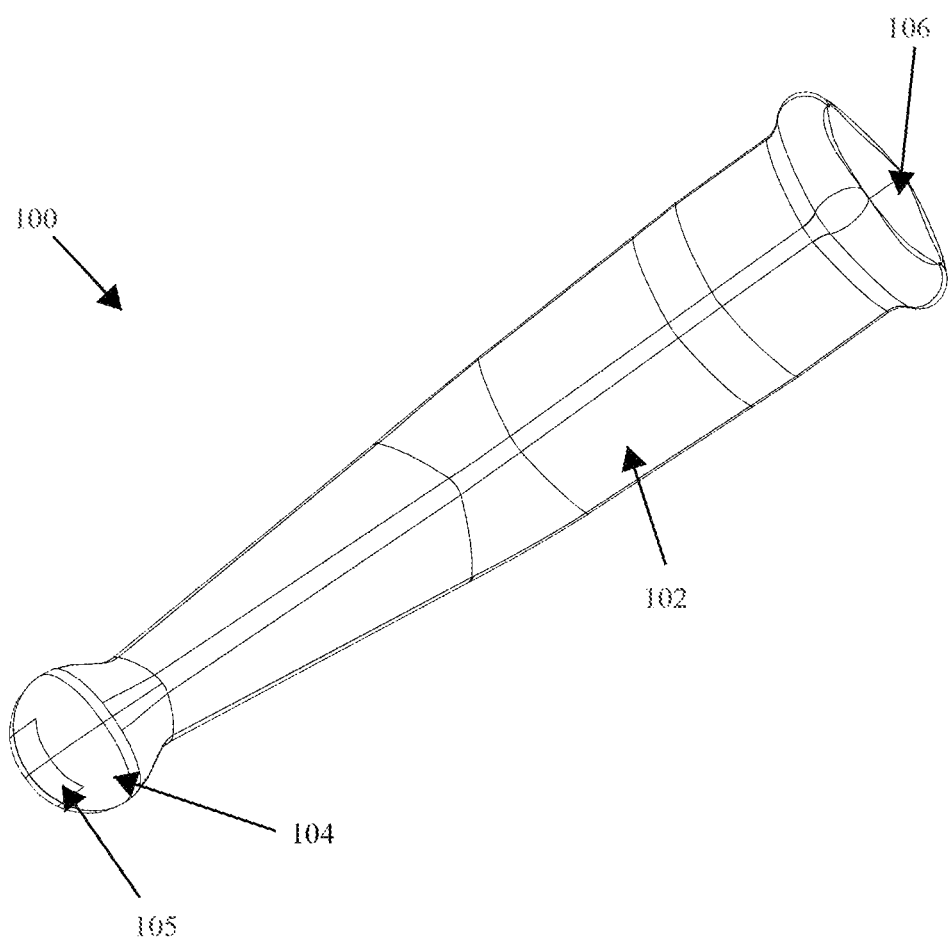
FIG. 1 represents an eyedrop container adapter, according to one embodiment of the present invention.
Figure 2:
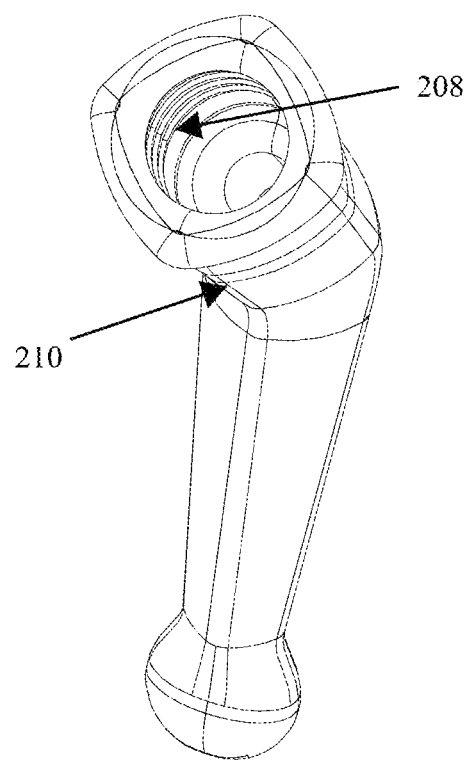
FIG. 2 represents bottom perspective view of the eyedrop container adapter, according to one or more embodiments of the invention.
Figure 3:
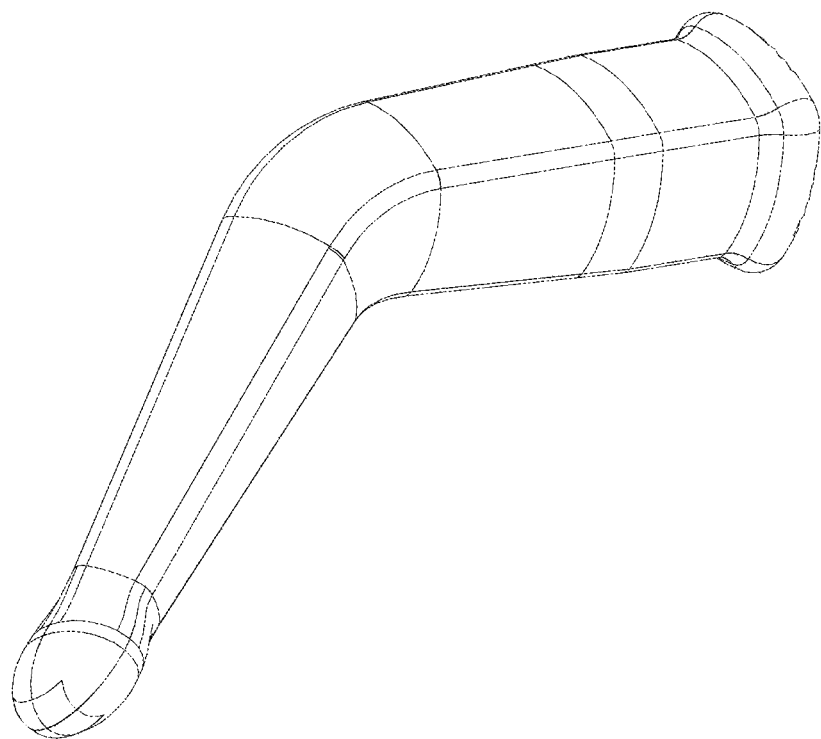
FIG. 3 represents the side perspective of the eyedrop container adapter, according to one or more embodiments of the invention.

FIG. 1 represents an eyedrop container adapter (100), according to one of the embodiment of the present invention. The present invention discloses an innovative eyedrop container adapter having an outer body (102), (106) opening for connecting with the container, (104) is the rounded tip incorporating the one-way valve (105) for dispensing the eyedrop. The various elements of the eyedrop adapter is described below with various features to enhance ease of use and hygiene. The below provides the list of structural elements and features of the eyedrop container adapter which are illustrated in FIG. 2 and FIG. 3.

One-way valve (105) at the tip to prevent backflow: The one-way valve is a critical component situated at the top of the apparatus. Its primary function is to ensure that once a drop of the eye solution is dispensed, there is no backflow into the container. This not only maintains the integrity of the remaining solution by preventing contamination but also contributes significantly to the overall hygiene of the eyedrop administration process.

Decreased internal lumen to reduce wastage of drops: The internal lumen refers to the space within the apparatus through which the eye solution travels during administration. By decreasing the internal lumen, the design aims to minimize the amount of solution wasted. The progressive narrowing also allows for a universal fit on most eyedrop containers. This reduction in wastage is not only economical but also ensures that the prescribed dosage of the ocular therapeutic agent is accurately delivered, optimizing the therapeutic benefits of the treatment.

Controlled flow design: The controlled flow design involves a mechanism that enables precise control over the dispensing of eye drops. The progressively narrowing lumen and the flat round disc tip allows a graduated exit of the eye drop, resulting in the formation of a drop that adheres to the tip. This feature is instrumental in flow control of the therapeutic agent, providing users with the ability to administer the solution with accuracy and confidence. This controlled flow is particularly beneficial for individuals requiring a steady and measured application of the ocular therapeutic agent.

Spiral grooves (208) at the base to ensure a snug fit and no outflow from the base: The base of the apparatus is equipped with spiral grooves, which serve a dual purpose. These grooves ensure a secure attachment to a variety of eyedrop containers, promoting universality in compatibility. Simultaneously, the grooves act as a safeguard against outflow between the adapter and the tip of the eye drop container, preventing any unintended leakage of the eye solution. This feature adds an extra layer of reliability to the apparatus, assuring users of a secure and mess-free administration process.

The device is manufactured with an antimicrobial material which can be augmented silicone or any other material having antimicrobial properties. The use of antimicrobial material in the construction of the apparatus is a strategic choice to address concerns related to hygiene. One possible material which is silicone augmented with specific metals, and is known for its antimicrobial properties. This significantly mitigates the risk of infections associated with the usage of this device by reducing microbial colonization.

Bent angle (210) to mitigate the risk of eye injury: The incorporation of a bent angle in the design is a safety-oriented feature. This specific curvature is intended to minimize the risk of potential eye injuries during the administration process. By introducing a bent angle, the design aims to enhance user safety by reducing the likelihood of accidental contact between the apparatus and the eye.

Rounded tip (104) to mitigate the risk of eye injury: The rounded tip serves as an additional safety measure, further mitigating the risk of eye injury during use. The smooth, flat, rounded design eradicates sharp edges that could potentially cause discomfort or harm during the application of eye drops. This feature prioritizes user safety and contributes to a more comfortable and secure user experience. The flat design is also a feature of controlling the flow of the exiting eyedrop.

There is a flowchart for process of administration using the eyedrop container, according to the present invention. The process of administering eye drops using the described apparatus involves a series of steps designed for compatibility, hygiene, and user safety:

First Step: Attach to Eyedrop Container: Begin by securely attaching the apparatus to the top of the eyedrop container, twisting to ensure a firm fit. The design of the apparatus, including the spiral grooves at the base, ensures a snug fit on a variety of eyedrop containers, promoting universality in compatibility. This step is crucial for users who may have different brands or types of eyedrop containers, providing them with a versatile solution for their eye care needs.

Next Step: Clean with a Sterile Wipe: Prior to each use, it is recommended to clean the apparatus and the receiving periorbital region with a sterile wipe. This step underscores the importance of maintaining a sterile environment during the eye drop administration process. Keeping the adapter and receiving periorbital region free from contaminants ensures that the eye solution remains pure and uncontaminated, reducing the risk of infections or adverse reactions. This emphasis on cleanliness aligns with best practices in ophthalmic care.

Next Step: Squeeze to Have a Drop Appear at the Round Tip: Once the apparatus is securely attached and cleaned, the next step involves the user squeezing the eye drop container. The design of the adapter allows users to have precise control over the amount of solution being dispensed, minimizing wastage, and ensuring an accurate dosage for effective treatment. This design allows the drop to stay on the device rather than falling off prior to contact with the periorbital region.

Optional Step: Head posturing. However, a proper head posture will ensure the use of the device in a more convenient and effective manner.

Next Step: Touch Lateral Canthus with Rounded Tip, and User will blink. With a drop of the eye solution present at the rounded tip, the user is instructed to touch the lateral canthus of the eye. The lateral canthus is the outer corner where the upper and lower eyelids meet. By touching this area with the rounded tip, user initiates the application process. Subsequently, the user blinks multiple times for the eye drop to completely fall on the ocular surface. This blinking action utilizes surface tension and a lateral-to-medial movement of eyelid closure to bring the drop onto the surface of the eye. The specific design elements, such as the bent angle and rounded tip, contribute to user safety during this step.

In summary, the described process emphasizes compatibility, effectiveness, hygiene, and safety throughout each stage of eye drop administration. The user-friendly features of the apparatus, coupled with the detailed steps, aim to provide a streamlined and effective solution for individuals seeking a hygienic and safe method for administering eye drops.

Advantages of the Present Disclosure

The described eyedrop container adapter presents several advantages that contribute to an improved and user-friendly experience in eye drop administration:

Hygiene Assurance: The one-way valve at the top prevents backflow, ensuring that the eyedrop solution remains uncontaminated within the container. This feature enhances hygiene by reducing the risk of introducing external contaminants into the solution.

Reduced Wastage: The decreased internal lumen minimizes the wastage of drops during administration. This not only makes the eyedrop application more economical but also ensures that the prescribed dosage is effectively delivered, maximizing the therapeutic benefits of the ocular therapeutic agent.

Precision and Controlled Dispensing: The controlled flow design provides users with precise control over the dispensing of drops. This feature enhances accuracy, allowing users to administer the eye solution in an effective, controlled, and measured manner, reducing the likelihood of overuse or spillage.

Universal Compatibility: The spiral grooves at the base ensure a secure fit on various eyedrop containers, promoting universal compatibility. This feature caters to users who may have different brands or types of eyedrop containers, offering a versatile solution that adapts to different container designs.

Microbial Resistance and Cleanliness: The use of silicone material in the construction of the adapter mitigates the risk of microbials, maintaining a clean and sterile environment for the eye solution. This feature contributes to the overall cleanliness and safety of the eye drop administration process.

Enhanced User Safety: The bent angle and rounded tip are designed to mitigate the risk of eye injury during application. These safety features prioritize user well-being, providing a comfortable and secure experience, especially important for individuals with sensitivity or concerns about accidental contact.

User-Friendly Application Process: The detailed process of attaching the adapter, cleaning it with a sterile wipe, squeezing to dispense a drop, and utilizing surface tension and eyelid movement for effective application is designed to be user-friendly. The streamlined process contributes to ease of use, making the administration of eye drops more effective for a wide range of users.

Efficient Surface Application: The process of touching the lateral canthus and relying on the user's blinking action to bring the drop onto the eye surface utilizes natural eyelid movements and surface tension. This enhances the effectiveness of the application, promoting effective coverage of the eye with the administered solution.

The invention claimed is:

1. An eyedrop adapter comprising:
a one-way valve positioned at the tip of the adapter to prevent backflow;
an internal lumen with a progressively decreasing diameter to improve fit and minimize wastage of drops during administration, optimizing the utilization of the ocular therapeutic agent;
a controlled flow design mechanism of a flat round disc tip and the progressively decreasing internal lumen, allowing for precise control over the dispensing of drops and preventing accidental spillage;
one or more spiral grooves at the base of the adapter, ensuring a secure attachment to various eyedrop containers and preventing unintended outflow, thereby minimizing the risk of leaks;
a bent angle is incorporated into the design to mitigate the risk of eye injury during the administration process, prioritizing user safety; and
the flat round disc tip encompassing the lumen that is transiting the entire diameter of the disc tip, terminating at the one-way valve, is designed to further minimize the risk of eye injury and enhance user safety during use.

2. The eyedrop container adapter of claim 1, wherein the adapter is constructed from an antimicrobial material, rendering it resistant to microbial growth, contributing to the maintenance of a clean and hygienic environment for the ocular therapeutic agent.

3. The eyedrop container adapter of claim 1, wherein said adapter is configured to attach to most eyedrop containers, ensuring compatibility with most containers.

4. The eyedrop container adapter of claim 1, wherein said adapter is further configured to be cleaned with a sterile wipe, together with the intended receiving periorbital region, emphasizing the importance of maintaining a sterile environment for eye health.

5. The eyedrop container adapter of claim 1, wherein said controlled flow design mechanism enables users to squeeze a container attached to the adapter, causing a drop to appear at the rounded tip for controlled and precise dispensing of the eyedrop.

6. The eyedrop container adapter of claim 1, wherein said rounded tip is designed to be touched to the lateral canthus during administration, facilitating a controlled application process where the user blinks to utilize surface tension and a lateral-to-medial movement of eyelid closure to bring the drop onto the ocular surface.

7. A method for administering eye drops using a universal eyedrop container adapter, the method comprising the steps of:

attaching the eyedrop container adapter securely to the top of an eyedrop container containing an eye medicine, ensuring compatibility with various container designs through the use of spiral grooves;

wherein the eyedrop container adapter comprises a controlled flow design mechanism of a flat round disc tip and a progressively decreasing internal lumen;

cleaning the adapter and receiving periorbital region with a sterile wipe before each use, emphasizing the importance of maintaining a sterile environment for eye health;

squeezing the container to facilitate the appearance of an eyedrop at a flat round disc tip encompassing the lumen that is transiting the entire diameter of the disc tip, terminating at a one-way valve, utilizing the controlled flow design mechanism for precise dispensing of the eyedrop;

head posturing to ensure the user's head is in a correct posture to receive the eye medicine;

touching the rounded tip of the adapter to the lateral canthus of the eye, initiating the administration process;

in response to the touch, blinking the eye to utilize surface tension and a lateral-to-medial movement of eyelid closure, bringing the eyedrop onto the surface of the eye.

8. The method of claim 7, further comprising the step of:

ensuring a secure fit of the adapter on the eyedrop container through the spiral grooves at the base, preventing unintended outflow and maintaining a clean administration process.

9. The method of claim 7, wherein the progressively decreasing internal lumen of the adapter minimizes the wastage of drops during administration, optimizing the utilization of the ocular therapeutic agent.

* * * * *